United States Patent [19]

Bowers et al.

[11] Patent Number: 4,704,193

[45] Date of Patent: Nov. 3, 1987

[54] COVALENTLY COUPLED COFACTOR MODIFIED ELECTRODES AND METHODS OF SYNTHESIS AND USE

[75] Inventors: Mark L. Bowers, Watertown; Mark A. Druy; Charles N. Durfor, both of Arlington; H. Gilbert Smith, Littleton; Sukant K. Tripathy, Arlington, all of Mass.; Barbara A. Yenser, Manchester, N.H.

[73] Assignee: GTE Laboratories Incorporated, Waltham, Mass.

[21] Appl. No.: 862,951

[22] Filed: May 14, 1986

[51] Int. Cl.$^4$ ............................................. B01D 59/40
[52] U.S. Cl. .................................. 204/1 T; 204/403; 204/418; 435/817; 435/291
[58] Field of Search ................... 204/290 R, 403, 1 T, 204/418; 427/58, 77, 338, 414; 435/817, 291

[56] References Cited

U.S. PATENT DOCUMENTS

| | | | |
|---|---|---|---|
| 4,321,123 | 3/1982 | Nakamura et al. | 204/403 |
| 4,357,142 | 11/1982 | Schall, Jr. et al. | 204/403 |
| 4,414,080 | 11/1983 | Williams et al. | 204/290 R |
| 4,439,302 | 3/1984 | Wrighton et al. | 204/290 R |
| 4,461,691 | 7/1984 | Frank | 204/290 R |
| 4,490,464 | 12/1984 | Gorton et al. | 204/403 |
| 4,528,270 | 7/1985 | Matsunaga | 204/403 |
| 4,532,188 | 7/1985 | Naarmann et al. | 204/290 R |
| 4,548,696 | 10/1985 | Weaver, Jr. | 204/290 R |
| 4,579,642 | 4/1986 | Niiyama et al. | 204/403 |
| 4,581,336 | 4/1986 | Malloy et al. | 204/403 |
| 4,582,805 | 4/1986 | Bozzelli et al. | 435/180 |
| 4,593,004 | 6/1986 | Boross et al. | 435/181 |
| 4,595,479 | 6/1986 | Kimura et al. | 204/294 |
| 4,609,600 | 9/1986 | Heinze et al. | 429/197 |
| 4,619,754 | 10/1986 | Niki et al. | 204/290 R |

OTHER PUBLICATIONS

Walker et al., *Eur. J. Biochem.*, 26, 279 (1972).
Frost et al., *J. Am. Chem. Soc.*, 102, 7157 (1980).
Wingard et al., "Flavins and Flavoproteins", p. 893, Walter de Gruyter & Co., Berlin & N.Y. (1984).
Miyawaki et al., *Biochimica et Biophysica Acta*, 838, 60 (1985).
Williamson et al., *Biochem.*, 24, 7790 (1985).
Wingard et al., *Biotechnology and Bioengineering Symp.*, 8, 483 (1978).
Wingard, *Trends in Analytical Chemistry*, 3, 235 (1984).
Varfolomeyev et al., *J. Molecular Catalysis*, 27, 305 (1984).
Castner et al., *Biochemistry*, 23, 2203 (1984).
Wieck et al., *Analytica Chimica Acta*, 158, 137 (1984).
Wrighton, *Science*, 231, 32 (1986).
Bootsma et al., *J. Polymer Sci: Polymer Chemistry Edn.*, 22, 705 (1984).
Foulds et al., *Bioessays*, 3, 129 (1985).
Bourdillon et al., *J. Electrochem. Soc.: Electrochemical Science and Technology*, 133, 706 (1986).

*Primary Examiner*—John F. Niebling
*Assistant Examiner*—Kathryn Rubino
*Attorney, Agent, or Firm*—Frances P. Craig

[57] ABSTRACT

An electrically and covalently coupled cofactor modified electrode for mediating the heterogeneous or homogeneous catalysis of a biochemical reaction by an enzyme. The electrode coating comprises an imidazole-flavin derivative covalently bonded to the electrode surface. Methods for preparation and use of the modified electrode are also presented.

27 Claims, 1 Drawing Figure

Fig. 1

COVALENTLY COUPLED COFACTOR MODIFIED ELECTRODES AND METHODS OF SYNTHESIS AND USE

This invention was made as a result of work under Contract No. MDA-903-85-C-0031 awarded by the U.S. Department of the Navy. The Government has certain rights in this invention.

THE FIELD OF THE INVENTION

This invention relates to heterogeneous and homogeneous catalyses by immobilized or soluble enzymes in a biochemical reaction and, more particularly, to a covalently and electrically coupled flavin cofactor modified electrodes and methods for electrochemically mediating such catalyses, as well as to methods for producing the cofactor modified electrode.

BACKGROUND OF THE INVENTION

In recent years, industrial applications for immobilized enzymes have grown dramatically, for example, in the diverse fields of fine pharmaceutical synthesis, clinical analysis, and in the production of bulk chemicals. However, the majority of industrial enzymes perform one of only three reactions: isomerization, hydrolysis or oxidation. None of these industrial enzymatic processes involves biological endothermic synthesis, and thus the utility of biological catalysts has been greatly limited. Attempts have been made to overcome this limitation by finding a way to artificially generate high-energy, nonphysiological and biological electron sources, including enzyme cofactor electron sources. Energy requiring enzymes such as formate dehydrogenase, hydrogenase, or nitrogenase could then be used in the synthesis of fuel or other important chemicals and in highly specific electrochemical sensors.

In order to catalyze a biochemical reaction involving one or more biochemical substrates, an enzyme must be capable of effecting electron transfer to or from the substrates. However, the amino acids which form the protein moieties of enzymes (the apoenzymes) cannot undergo changes in redox state. Therefore, all redox active enzymes require nonprotein, redox active organic, metal or metal-organic cofactors in order to perform these biological electron transfers. There exist several types of cofactors to accomplish a variety of electron transfer processes, each apoenzyme requiring a specific cofactor for activation.

In nature, electron transfer processes occur either between two protein-found cofactors or between a protein-bound cofactor and some small metabolic compound. Among the most versatile of the redox active cofactors are the flavin nucleotides which are involved both in transfer-ring charge between protein-bound cofactors and in catalyzing metabolic redox changes. The flavin cofactors are unique because they can transfer either single or pairs of electrons. Flavin cofactors form an integral part of the redox active sites of many different enzymes. In these enzymes the apoenzyme confers specificity to the reaction, permitting only specific chemicals to arrive at the active site. Thus, a given cofactor can perform several different processes depending on the protein environment at a specific active site. These redox active flavin cofactors are derived from flavin compounds having the formula in which $R_1$ is a ribose derivative; e.g. riboflavin (RF), flavin mononucleotide (FMN) and flavin adenine dinucleotide (FAD). In natural systems FMN and FAD allow the required electron transfer between substrates.

Attempts have been made to provide electrochemical control of such biochemical reactions and regeneration of the flavin cofactor's redox state by coupling the natural system (e.g. the cofactor, apoenzyme and substrate) with an electronic assembly (e.g. an electrode and a current source). These attempts include: (1) providing an intermediate mobile carrier to shuttle electrons between the electrode and the enzyme in solution; (2) physically or chemically immobilizing the enzyme in a gel and/or by trapping it within a membrane or polymer to hold the enzyme in close contact with an electrode surface; and (3) adsorbing the enzyme on the surface of an electrode, either with or without a mediating compound. These methods, however, have the disadvantages of less than optimum electron transfer efficiency, diffusional resistance, chemical instability of the components, steric and electronic interference, and/or adherence problems.

As in designing any electrocatalytic system, a method must be found for rapidly and efficiently transporting charges between the electrocatalytic species (in this case the enzyme cofactor) and the electrode surface. Additionally, the biochemical substrate must be free to interact with the electrocatalytic species without steric or electronic interference. Thus, a need exists for a means of achieving a more direct electronic linkage between the electrode and the active site of the enzyme in order to effect efficient energy transfer for the catalysis of many biochemical reactions.

Prior to the present invention, it has been theorized that this could be achieved by covalent attachment of the enzyme to the activated surface of an electrode, either directly or through a mediating compound and/or a spacer compound. For example, Miyawaki et al. (*Biochemica et Biophysica Acta*, 838, p. 60, 1985) report covalently coupling FAD to a glassy carbon electrode at the FAD adenine amino group or a ribityl —OH group, either with or without spacer compounds. The immobilized cofactor was shown to catalyze the oxidation of NADH, but no reconstitution of enzyme activity occurred when the apoenzyme of glucose oxidase was added to the system.

The orientation of the cofactor in the enzyme has been found to be critical for the proper functioning of the enzyme. For example, it is usually found that the flavin cofactors must be oriented with the benzenoid end of the flavin cofactor projecting into the solution, while the other, heterocyclic end is surrounded by the apoenzyme.

Attempts have been made to avoid steric and electronic interference by coupling the flavin cofactor to the electrode surface at the flavin 8-alpha methyl position. For example, L. B. Wingard, Jr. et al. (Flavins and Flavoproteins, p. 893, Walter de Gruyter & Co., Berlin, New York, 1984) claim to have (1) attached riboflavin to the surface of a glassy carbon electrode by reacting 8-bromoflavin with n-butyllithium, then (2) converted the riboflavin to FMN and subsequently to FAD, and finally (3) incubated the modified electrode with the apoenzyme of glucose oxidase. A small degree (0.0021 units/electrode) of biological activity was reported. However, prior to the present invention, such electrodes have required strongly basic coupling conditions, have exhibited a low biological activity level, and have been subject to breakdown of the chemical bond at the 8-alpha methyl position of the flavin moiety when exposed to even weakly basic environments.

The successful formation of an efficient, biologically active, chemically stable, covalently and electrochemically coupled flavin cofactor modified electrode would provide the basis for the development of an entirely new class of bioelectronic detectors and catalysts. Further, the use of an appropriate means of linking the electrode surface and the cofactor would allow large active surface coverages of the cofactor-mediators and encourage effective electron transfer from the electrode to the enzyme by presenting a low energy barrier to such transfer due to the short, low resistance distance (less than 10 angstroms) between the electrode and the enzyme. Monitoring the current flow from an electrode with a protein renatured on its surface or a flavoprotein or holoenzyme in solution would allow specific quantitation (due to enzymatic specificity) of analytes by convenient electronic methods. Further, using the electrode to maintain the biological cofactor at a specific potential would permit biocatalytic reactions to be driven by electrochemical energy without the need for additional expensive biological energy sources, e.g. redox active cofactors.

SUMMARY OF THE INVENTION

The present invention presents to the art novel, stable and more efficient cofactor modified electrodes and methods for electrochemically interfacing an enzyme to an electrode, overcoming the above-described limitations, as well as methods of preparing the novel electrodes.

The electrodes and methods of the present invention involve coupling biological and electronic processes to effect electron transfer between an electrode and one or more biochemical substrates by activating an enzyme selected to catalyze the reaction at a working surface of the electrode through a suitable redox active flavin cofactor bonded to the electrode.

A cofactor modified electrode, according to one aspect of the invention, comprises an electrode having a working surface of an electrically conducting or semi-conducting material having an outer oxide or hydroxyl containing layer; and a redox active material covalently and electrically bonded to the outer layer of the electrode surface by means of a suitable linking group, preferably a silane derivative. The redox active material is derived from a redox active flavin derivative having the formula wherein $R_1$ is a ribose derivative, preferably —$CH_2$(-$CHOH)_3CH_2OH$, —$CH_2(CHOH)_3CH_2O$—$PO_3^{2-}$, —$CH_2(CHOCOCH_3)_3CH_2OCOCH_3$, or at least one of $R_2$ and $R_3$ is an imidazole derivative, preferably and the other of $R_2$ and $R_3$ is the imidazole derivative or hydrogen. The redox active material may be oriented to permit coupling of its flavin cofactor moiety to a suitable apoenzyme in solution to form a renatured enzyme and to permit electron transfer between the electrode surface and the renatured enzyme, or to permit interaction of the flavin cofactor moiety with an enzyme in solution to permit electron transfer to activate the enzyme. The cofactor-to-electrode surface linkage is selected to allow the immobilized cofactor to retain its bioactivity.

A preferred cofactor modified electrode has a working surface of platinum, gold, silicon, graphite, glassy carbon or a conducting polymer having an outer oxide or hydroxyl layer, or tin dioxide. Electrically and covalently bonded to the outer layer is a coating comprising groups of the formula wherein $R_1$ is a ribose derivative as described above, the silane is bonded to the imidazole moiety at the N-3, C-4 or C-5 position on the imidazole ring, and $R_7$ and $R_8$ are each independently an $—O—C_2H_5$ group, a hydroxyl group, or an —O— link to an adjacent silane group or to the outer layer of the electrode surface.

According to another aspect of the invention, a method of effecting electron transfer between an electrode having a working surface of an electrically conducting or semiconducting material and an enzyme comprises modifying the working surface of the electrode by electrically and covalently bonding a redox active material to an existing or derivatized outer oxide or hydroxyl layer on the working surface, by means of a suitable linking group. The redox active material is derived from a redox active flavin derivative having the formula in which $R_2$ and $R_3$ are as described above. The flavin cofactor moiety of the redox active flavin derivative is selected to activate the enzyme, i.e. $R_1$ is a ribose derivative selected to provide the selected flavin cofactor moiety. The modified working surface of the electrode is immersed in an electrolyte solution containing the enzyme or the protein moiety of the enzyme, and an electric potential is applied to the electrode sufficient to effect the electron transfer between the electrode surface and the enzyme through the redox active material.

A method of electrochemically mediating the catalysis of a reaction involving one or more biochemical substrates by an enzyme, according to another aspect of the invention, comprises modifying the working electrode as described for the above method, and establishing in an electrochemical cell, having at least the modified electrode and an auxiliary electrode, an electrolyte solution containing the one or more biochemical substrates and an enzyme or the protein moiety of an enzyme suitable for catalyzing the reaction. An electric potential is applied to the electrodes sufficient to effect electron transfer between the electrode and the biochemical substrate through the redox active material and the enzyme.

According to yet another aspect of the invention, a method for coating an electrode substrate having a working surface of an electrically conducting or semiconducting material having an outer oxide or hydroxyl layer comprises electrically and covalently bonding a redox active material to the outer layer by means of a suitable linking group. The redox active material is derived from a redox active flavin derivative having the formula in which $R_1$, $R_2$ and $R_3$ are as described above.

According to still another aspect of the invention, a method is presented for preparing a working electrode for electrochemically mediating the catalysis of a biochemical reaction by an enzyme. An electrode having a working surface of an electrically conducting or semiconducting material having an outer oxide or hydroxyl layer is placed within a vessel. The working surface of the electrode is immersed in an electrolyte solution containing a redox active flavin derivative and a compound from which a suitable linking group may be derived, for a sufficient time to electrochemically and covalently bond sufficient redox active material to the outer layer of the working surface, by means of the linking group, to provide a working electrode capable of electrochemically mediating the catalysis of the biochemical reaction.

The flavin derivative has the formula in which $R_1$ is a ribose derivative, preferably: $—CH_2(CHOH)_3CH_2OH$, $—CH_2(CHOH)_3CH_2O—PO_3^{2-}$, $—CH_2(CHOCOCH_3)_3CH_2OCOCH_3$, or and at least one of $R_2$ and $R_3$ is an imidazole derivative, preferably:

while the other of $R_2$ and $R_3$ is the imidazole derivative or hydrogen. The preferred linking group is a silane compound of the formula in which $R_4$, $R_5$ and $R_6$ are independently selected from the Si ligands displaceable by a hydroxide anion, and n is a positive integer from 1 to 20. The electrode is immersed in the solution for a sufficient time to electrochemically and covalently bond sufficient redox active material to the outer layer on the working surface, by means of the linking group, to provide a working electrode capable of electrochemically mediating the catalysis of the biochemical reaction. In a preferred method, the vessel is an electrochemical cell also containing an auxiliary electrode. An electrical potential is established across the electrodes during the electrical and covalent bond formation.

The covalent bonding to the electrode surface of a prepared, site-specific imidazole derivative of the flavin cofactor, linked at the 7-alpha methyl or 8-alpha methyl position on the cofactor's structure, leaves the electron transport properties and bioactivity capabilities of the biological cofactor intact and, equally important, provides chemical stability to the modified electrode by protecting the flavin's 7-alpha methyl or 8-alpha methyl covalent bond from chemical attack.

BRIEF DESCRIPTION OF THE DRAWING

For a better understanding of the present invention, together with other objects, advantages and capabilities thereof, reference is made to the following Description and appended claims, together with the Drawing, in which:

DETAILED DESCRIPTION OF PREFERRED EMBODIMENTS

A cofactor modified electrode according to the invention comprises a flavin cofactor moiety, for example a tetracetylriboflavin derivative, and an imidazole moiety, for example imidazole, electrically and covalently bonded to an electrically conducting or semiconducting working surface of an electrode by means of a suitable linking group. The linking group is preferably a silane group, for example a derivative of $(C_2H_5O)_3Si(CH_2)_3$—NCO. The working surface of the electrode is derivatized by known means to provide an outer oxide or hydroxyl layer to which the imidazole-flavin derivative may be covalently bonded. Various electrode surface materials as well as other bonding groups are possible, and are within the scope of this invention; for example, graphite or glassy carbon, platinum, gold, silicon, tin dioxide or a conducting polymer with derivatives of other alkoxy(isocyanato)-silanes or other silane compounds, or with conducting polymers with attendant hydroxy groups.

The preferred flavin cofactor moiety is derived from a flavin derivative having a ribose derivative moiety of the formula:

—$CH_2(CHOH)_3CH_2OH$, —$CH_2(CHOH)_3C-H_2O$—$PO_3{}^{2-}$,

—$CH_2(CHOCOCH_3)_3CH_2OCOCH_3$, or

Thus the preferred flavin moiety is a derivative of a riboflavin (RF), flavin mononucleotide (FMN), tetracetyl riboflavin (TARF), or flavin adenine dinucleotide (FAD), respectively. The preferred imidazole moiety is selected from derivatives of imidazole, histamines and histadines of the formulas:

The flavin cofactor moiety is attached to the imidazole moiety through the 7-alpha methyl or 8-alpha methyl position of the flavin, preferably to the N-1 position of the imidazole ring. This linking of the flavin group and imidazole group must be accomplished, e.g. by known means, to form a redox active flavin derivative before the redox active flavin derivative is attached to the electrode as a covalently bonded coating on its surface. This type of imidazole-flavin compound may be synthesized, for example, by the procedures described by Walker et al. (*Eur. J. Biochem.* 26, No. 2, 279 (1972)), by Frost et al. (*J. Am. Chem. Soc.* 102, 7157 (1980)) and by Williamson et al. (*Biochem,* 24, 7790 (1985)). Use of the prepared imidazole-flavin derivative to form a redox active coating on the electrode provides chemical stability to the covalent bond linking the flavin and imidazole moieties, and allows significantly milder coupling conditions than described by Wingard, Jr. et al., referenced above.

Using an imidazole derivative as the bridge between the electrode surface and the covalently bonded enzyme cofactor permits: (1) site specific coupling of the flavin moiety to the electrode surface, (2) significantly retarded flavin decomposition due to milder surface derivatization conditions, (3) high concentration of the imidazole-flavin on the electrode surface, and (4) rapid and efficient charge transfer between the electrode and the enzyme. Thus, the present invention achieves the benefits of both stable immobilization of the enzyme cofactor and rapid electron transfer.

Electrical activity may be observed if the cofactor moiety is sterically or electronically hindered. However, the orientation of the cofactor moiety on the coated electrode for effective coupling of the cofactor to the active site of the enzyme is critical to the efficient bioactivity of the modified electrode. The benzenoid end of the flavin cofactor is linked to the oxide or hydroxyl layer of the electrode working surface through the imidazole intermediate and a suitable linking group, freeing the heterocyclic end of the cofactor to be incorporated into or interact with the electroactive site of the enzyme. Rapid, efficient, and controlled electron transfer to or from the one or more biochemical substrates and regeneration of the cofactor's redox state are then effected by the electric potential applied to the electrode. Thus, a path for electron transfer is established between the electrode and the substrate(s) by way of the redox active coating.

The provision of a coating of a redox active material on an electrode surface, according to the invention, makes possible the method of this invention. A coated working electrode, for example a platinum electrode coated with the imidazole-flavin redox active material described above, is introduced to an electrochemical cell containing an electrolyte solution including one or more biochemical substrates and an enzyme capable of being activated by the cofactor moiety of the coated electrode, and suitable for catalyzing a desired biochemical reaction involving the substrate(s). When an electric potential is applied to the working electrode, electron transfer takes place between the working surface of the electrode and the enzymatic cofactor covalently bonded thereto. The direction in which the electron movement takes place depends on whether the working electrode is established as a cathode or as an anode.

The enzyme may be present in the solution as an apoenzyme, i.e. the protein moiety of the enzyme, or a holoenzyme, i.e. a complete enzyme, may be present in the solution or immobilized on the electrode surface in known manner. However, the enzyme must be capable of being activated by the cofactor moiety and be suitable for catalyzing the reaction.

The transfer of charge between the electrode and the cofactor is utilized to electrochemically generate the necessary form of the cofactor to activate the protein moiety of the enzyme in solution or renatured on the electrode working surface or, in the case of a holoenzyme in solution or immobilized on the electrode surface, to regenerate the redox state of the cofactor incorporated in the holoenzyme. The activated enzyme is then able to bind the specific biochemical substrate(s) to its active site, thus making possible the catalysis of the desired biochemical reaction involving the substrate(s).

For apoenzymes further requiring metal ions for activation, the appropriate metallic ions may be provided, if necessary, in the electrolyte solution within the electrochemical cell. The metallic ions in solution may be bound to the active site of the enzyme to complete activation of the enzyme.

The modified electrodes of the invention, the method of producing the electrodes and the use of such electrodes may be more completely understood by referring to the following Examples.

EXAMPLE 1

Preparation of the cofactor modified electrode

The working surface of a teflon shrouded platinum electrode (available from Bioanalytical Systems Inc., West Lafayette, IN) was polished with a 0.3 micron alumina suspension (available from Fisher Co., Medford, MA) on a felt pad. The freshly prepared electrode was then established as the working electrode in a standard two-compartment electrochemical cell having a glass frit separating the chambers. A platinum counter electrode and a standard calomel (SCE) reference electrode were also used.

Also preparation procedures were performed under ambient conditions. Tetraacetyl-8-alpha-imidazoleflavin (TIF) was synthesized by the method described by Williamson et al., referenced above.

A solution of 20 mM of TIF and 0.1M LiClO$_4$ supporting electrolyte in methanol containing about 5 volume % water was added to the working electrode compartment of the electrochemical cell. While cycling the potential between 0.0 and $-0.6$ V, sufficient 3-isocyanatopropyltriethoxysilane (ICPS; available from Petrarch Systems, Inc., Bristol, PA) was added to the TIF solution to yield a final concentration of 30 mM. After cycling for 10–30 min. after the addition of the ICPS, the TIF cofactor modified electrode was removed from the cell and rinsed with ethanol. Alternatively, the electrodes may be dried for 24 hrs. prior to use.

Characterization and testing of the cofactor modified electrode

All electrochemical measurements were made in a single compartment electrochemical cell, under anaerobic ambient conditions, and using a platinum counter electrode and a SCE reference electrode.

Figure 1:
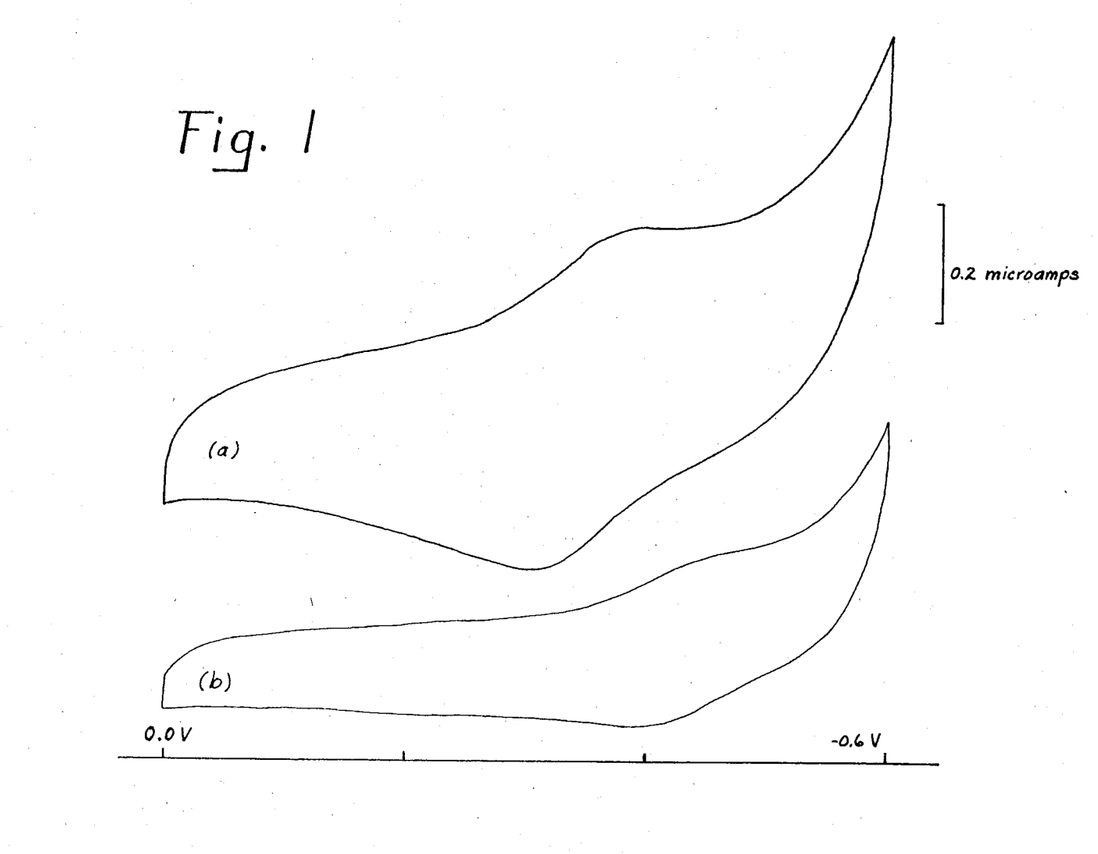
FIGS. 1a and 1b are tracings of actual cyclic voltammetric responses of two modifid electrodes in an electrolyte solution.

FIG. 1$a$ illustrates a cyclic voltammetric response in an aqueous solution of pH 6.5 (0.10M phosphate buffer and 0.50M KCl) for the TIF cofactor modified electrode at a scan rate of 100 mV/sec showing reversible electron transfer to and from the flavin cofactor moiety over many cycles. Approximately a monolayer of flavin coverage of the working surface of the electrode, $1.7 \times 10^{-11}$ moles/cm$^2$, was calculated from the charge under the oxidation wave of FIG. 1$a$ and the electrode surface area.

FIG. 1$b$ illustrates the cyclic voltammetric response under conditions identical to FIG. 1$a$ of a platinum electrode modified according to the process described for preparation of the TIF electrode, but with 20 mM FMN cofactor (without an imidazole moiety) replacing the TIF in the electrolyte solution. Comparison of FIGS. 1a and 1b demonstrates the importance of the imidazole functionality for efficient covalent modification of the electrode working surface. Despite the availability of the FMN ribose hydroxyl groups for reaction, little flavin is bound to the electrode working surface (as shown by the charge under the oxidation wave), as compared to the binding of the imidazole-flavin.

The coating formed was stable both to several hundred voltammetric scans and to sonication in water, methanol, or acetonitrile. When stored in the absence of light, the electrode was stable for at least two weeks. As expected for surface bound species, the magnitudes of the peak oxidation and reduction currents increased linearly with increasing scan rates from 5–500 mV/sec. At the 100 mV/sec scan rate illustrated in FIG. 1a, the reduction and oxidation peak current separation was 70 mV; while at 5 mV/sec a separation of only 5 mV was observed.

Similar voltammetric responses were obtained using TIF/ICPS modified gold and tin dioxide electrode surfaces. Also, TIF/ICPS modification of metal oxide surfaces was successfully achieved using the method described above but without application of an electrochemical potential to the electrodes. The concentration of flavin coverage was not affected, but the background responses of the modified electrodes not subjected to voltage cycling was higher. The working surface areas of the modified electrodes prepared and tested varied from 0.07 cm$^2$ to over 70 cm$^2$.

EXAMPLE 2

The TIF modified electrode may be further derivatized by known methods to convert the surface bound TIF moiety to imidazole-flavin monomucleotide (IFMN) or imidazole-flavin adenine dinucleotide (IFAD) moieties. Thus, the TIF electrode may be modified to produce electrodes with FMN or FAD functionalities respectively.

Conversion of the surface bound TIF to imidazole-flavin mononucleotide (IFMN)

The above TIF modified electrode was immersed in 0.1M HCl in aqueous solution for 1 hr under ambient conditions to achieve deacetylation of the ribose group by acid hydrolysis. Subsequently, the electrode was immersed in 5 to 1 POCl$_3$/water (v/v) solution for 1.5 hr at 4° C. The POCl$_3$ soltuion was allowed to come to room temperature and the electrode allowed to remain immersed for 3.5 hr to form a surface bound IFMN moiety by phosphorylation of the deacetylated ribose group. The IFMN electrode was then rinsed with distilled water and allowed to stand in distilled water at room temperature for 24 hr.

EXAMPLE 3

Catalysis of the oxidation of lactate by means of the apoenzyme of lactate oxidase renatured on the electrode surface The above IFMN modified electrode is then established as the working electrode in an electrolytic cell with a platinum auxiliary electrode and SCE reference electrode. The cell contains an anaerobic aqueous electrolyte solution of pH about 8.5, containing 0.5M KCl, phosphate buffer, and the substrate lactate at 100 micromolar. A potential of +0.020 V vs the SCE electrode applied between the electrodes, the voltage being selected to be higher than the thermodynamic potential necessary to oxidize the lactate but lower than the potential needed by the electrode in the absence of the enzyme lactate oxidase, results in little current flow.

The apoenzyme of lactate oxidase is added to the electrolyte solution to give a concentration of about 1 nanomoles of active sites available for catalysis of the reaction. The current increases substantially with addition of the apoenzyme, demonstrating that the covalently bound FMN cofactor is mediating the electron transfer from the modified electrode to lactate oxidase renatured on the surface of the electrode, therefore allowing it to oxidize lactate.

EXAMPLE 4

Catalysis of the oxidation of lactate by means of lactate oxidase holoenzyme in solution The procedure described in Example 3 is repeated, except that the TIF modified electrode of Example 1 is used as the working electrode and an equivalent amount of the holoenzyme of lactate oxidase replaces the apoenzyme in solution. Again, the current increases substantially with the addition of the holoenzyme. This increase in current demonstrates that the covalently bound flavin is mediating the electron transfer from the modified electrode to the lactate oxidase enzyme in solution, therefore allowing it to mediate the oxidation of lactate.

EXAMPLE 5

Catalysis of the oxidation of lactate by means of lactate oxidase holoenzyme immobilized on the electrode surface

The procedure of Example 4 is repeated, except that a small amount of the holoenzyme immobilized in known manner on the working surface of the TIF modified electrode replaces the holoenzyme added to the solution. The lactate oxidase is physically entrapped in an inert polyacrylamide gel and directly dispersed on the surface of a cellophane membrane having a pore size of 4–60 nm and a thickness of 0.127 mm. The membrane is secured to cover the modified working surface of the electrode, to provide physical contact between the flavin cofactor moiety of the electrode coating and the holoenzyme. The exact proportions of enzyme to gel are not critical, but the electrode assembly provides about $1 \times 10^{-11}$ moles/cm$^2$ of active sites. Yet again, the current increases substantially with the enzyme immobilized on the electrode as compared to the flavin modified electrode in electrolyte without the holoenzyme. This current increase demonstrates that the covalently bound flavin is mediating the electron transfer from the electrode to the immobilized enzyme, allowing it to catalyze the oxidation of lactate in the electrolyte solution.

The cofactor modified electrodes according to the invention are capable of interacting with a wide variety of enzymes. The flavin cofactors display wide versatility in interacting with biological systems. Hundreds of proteins are known to require a flavin cofactor at their catalytic center for activation. Thus the modified electrodes according to the invention, having an imidazole-flavin derivative covalently bonded to the electrode working surface, can provide direct and efficient electronic linkages to many types of biological catalytic sites. The flavin modified electrodes of the invention may be utilized as "generic" devices whose specificity is determined by the specific enzyme used in a particular application. Such electrodes and the methods for their preparation and use are expected to provide the basis for development of highly useful bioelectronic detectors and catalyst systems.

What is claimed is:

1. A cofactor modified electrode comprising:
   an electrode substrate having a working surface of an electrically conducting or semiconducting material having an outer oxide or hydroxyl containing layer; and
   a redox active material electrically and covalently bonded to the outer layer by means of a suitable linking group;
   wherein the redox active material is derived from a redox active flavin derivative having a flavin cofactor moiety, and having the formula wherein $R_1$ is a ribose derivative, and at least one of $R_2$ and $R_3$ is an imidazole derivative, the other of $R_2$ and $R_3$ being the imidazole derivative or hydrogen.

2. An electrode according to claim 1 wherein the redox active material is oriented to permit coupling of the flavin cofactor moiety to a suitable apoenzyme in a solution to form a renatured enzyme and to permit electron transfer between the electrode surface and the renatured enzyme.

3. An electrode according to claim 1 wherein the redox active material is oriented to permit electron transfer between the flavin cofactor moiety and a holoenzyme in a solution to activate the holoenzyme.

4. An electrode according to claim 1 wherein $R_1$ is selected from the group consisting of —CH$_2$(CHOH)$_3$CH$_2$OH, —CH$_2$(CHOH)$_3$CH$_2$O—PO$_3^{2-}$, —CH$_2$(CHOCOCH$_3$)$_3$CH$_2$OCOCH$_3$, and 5. An electrode according to claim 1 wherein the imidazole derivative is selected from the group consisting of

6. An electrode according to claim 1 wherein the working surface of the electrode is of a material selected from the group consisting of platinum, gold, tin dioxide, silicon, graphite, glassy carbon, and conducting polymers.

7. An electron according to claim 1 wherein the linking group is a derivative of a silane compound having the formula wherein $R_4$, $R_5$, and $R_6$ are independently selected from the group consisting of the Si ligands displaceable by a hydroxide anion, and n is a positive integer from 1 to 20.

8. A cofactor modified electrode comprising:
   an electode substrate having a working surface of an electrically conducting or semiconducting material selected from the group consisting of platinum, gold, silicon, graphite, glassy carbon, or tin dioxide, and conducting polymers and having an outer oxide or hydroxyl layer; and
   a redox active coating electrically and covalently bonded to the outer layer and comprising groups of the formula wherein $R_1$ is a ribose derivative selected from the group consisting of —CH$_2$(CHOH)$_3$—CH$_2$OH, —CH$_2$(CHOH)$_3$CH$_2$O—PO$_3^{2-}$, —CH$_2$(CHOCOCH$_3$)$_3$CH$_2$OCOCH$_3$, and —CH$_2$(CHOH)$_3$CH$_2$O—P—O—P—O—CH$_2$ the silane group is bonded to the imidazole moiety at the N-3, C-4 or C-5 position on the imidazole ring, and $R_7$ and $R_8$ are each an $-O-C_2H_5$ group, a hydroxyl group, or an $-O-$ link to an adjacent silane group or to the outer layer of the electrode surface, and may be the same or different.

9. A method of effecting electron transfer between an electrode having a working surface of an electrically conducting or semiconducting material and an enzyme comprising the steps of:

modifying the working surface of the electrode by electrically and covalently bonding to an existing or derivatized outer oxide or hydroxyl layer on the working surface, by means of a suitable linking group, a redox active material derived from a redox active flavin derivative having a flavin cofactor moiety, and having the formula wherein at least one of $R_2$ and $R_3$ is an imidazole derivative, the other of $R_2$ and $R_3$ being the imidazole derivative or hydrogen; and wherein the flavin cofactor moiety of the redox active flavin derivative is selected to activate a protein moiety of the enzyme, $R_1$ being a ribose derivative selected to provide the selected flavin cofactor moiety;

immersing the modified working surface of the electrode in an electrolyte solution containing the protein moiety of the enzyme; and applying an electric potential to the electrode sufficient to effect the electron transfer between the electrode surface and the enzyme through the redox active material.

10. A method according to claim 9 wherein $R_1$ is selected from the group consisting of $-CH_2(CHOH)_3CH_2OH$, $-CH_2(CHOH)_3CH_2O-PO_3^{2-}$, $-CH_2(CHOCOCH_3)_3CH_2OCOCH_3$, and the imidazole of derivative is selected from the group consisting of the working surface of the electrode is of a material selected from the group consisting of platinum, gold, tin dioxide, silicon, graphite, glassy carbon, and conducting polymers, and the linking group is a derivative of a silane compound having the formula wherein $R_4$, $R_5$ and $R_6$ are independently selected from the group consisting of Si ligands displaceable by a hydroxide anion, and n is a positive integer from 1 to 20.

11. A method of effecting electron transfer between an electrode having a working surface of an electrically conducting or semiconducting material and an enzyme comprising the steps of:

modifying the working surface of the electrode by electrically and covalently bonding to an existing or derivatized outer oxide or hydroxyl layer on the working surface, by means of a suitable linking group a redox active material derived from a redox active flavin derivative having a flavin cofactor moiety, and having the formula wherein at least one of $R_2$ and $R_3$ is an imidazole derivative, the other of $R_2$ and $R_3$ being the imidazole derivative or hydrogen; and wherein the flavin cofactor moiety of the redox active flavin derivative is selected to activate the enzyme, $R_1$ being a ribose derivative selected to provide the selected flavin cofactor moiety;

immersing the modified working surface of the electrode in an electrolyte solution in an electrochemical cell;

introducing the enzyme to the electrochemical cell; and applying an electric potential to the electrode sufficient to effect the electron transfer between the electrode surface and the enzyme through the redox active material.

12. A method according to claim 11 wherein the step of introducing the enzyme to the electrochemical cell comprises adding the enzyme to the electrolyte solution.

13. A method according to claim 11 wherein the step of introducing the enzyme to the electrochemical cell comprises immobilizing the enzyme on the working surface of the electrode.

14. A method according to claim 11 wherein $R_1$ is selected from the group consisting of —CH$_2$(CHOH)$_3$CH$_2$OH, —CH$_2$(CHOH)$_3$CH$_2$O—PO$_3{}^{2-}$, —CH$_2$(CHOCOCH$_3$)$_3$CH$_2$OCOCH$_3$, and the imidazole derivative is selected from the group consisting of

-continued the working surface of the electrode is of a material selected from the group consisting of platinum, gold, tin dioxide, silicon, graphite, glassy carbon, and conducting polymers, and the linking group is a derivative of a silane compound having the formula wherein $R_4$, $R_5$ and $R_6$ are independently selected from the group consisting of Si ligands displaceable by a hydroxide anion, and n is a positive integer from 1 to 20.

15. A method of electrochemically mediating the catalysis of a reaction involving one or more biochemical substrates by an enzyme comprising the steps of:

modifying a working surface of a working electrode by electrically and covalently bonding to an existing or derivatized oxide or hydroxyl layer on the working surface, by means of a suitable linking group, a redox active material derived from a redox active flavin derivative having a flavin cofactor moiety, and having the formula wherein at least one of $R_2$ and $R_3$ is an imidazole derivative, the other of $R_2$ and $R_3$ being the imidazole derivative or hydrogen; and wherein the flavin cofactor moiety of the redox active flavin derivative is selected to activate a protein moiety of the enzyme, $R_1$ being a ribose derivative selected to provide the selected flavin cofactor moiety;

establishing in an electrochemical cell having at least the modified electrode and an auxiliary electrode, an electrolyte solution containing the biochemical substrate(s) and the protein moiety of an enzyme suitable for catalyzing the reaction; and applying an electric potential to the electrodes sufficient to effect electron transfer between the modified electrode and the biochemical substrate through the redox active material and the enzyme.

16. A method according to claim 15 wherein the enzyme is a metalloenzyme and the electrolyte solution further contains one or more metallic ions suitable for coupling with the protein moiety and the flavin cofactor moiety to complete the enzyme.

17. A method according to claim 15 wherein $R_1$ is selected from the group consisting of —CH$_2$(CHOH)$_3$CH$_2$OH, —CH$_2$(CHOH)$_3$CH$_2$O—PO$_3{}^{2-}$, —CH$_2$(CHOCOCH$_3$)$_3$CH$_2$OCOCH$_3$, and the imidazole derivative is selected from the group consisting of the working surface of the electrode is of a material selected from the group consisting of platinum, gold, tin dioxide, silicon, graphite, glassy carbon, and conducting polymers, and the linking group is a derivative of a silane compound having the formula wherein $R_4$, $R_5$ and $R_6$ are independently selected from the group consisting of Si ligands displaceable by a hydroxide anion, and n is a positive integer from 1 to 20.

18. A method of electrochemically mediating the catalysis of a reaction involving one or more biochemical substrates by an enzyme comprising the steps of:

modifying a working surface of an electrode by electrically and covalently bonding to an existing or derivatized outer oxide or hydroxyl layer on the working surface by means of a suitable linking group, a redox active material derived from a redox active flavin derivative having a flavin cofactor moiety, and having formula wherein at least one of $R_2$ and $R_3$ is an imidazole derivative, the other of $R_2$ and $R_3$ being the imidazole derivative or hydrogen; and wherein the flavin cofactor moiety of the redox active flavin derivative is selected to activate the enzyme, $R_1$ being a ribose derivative selected to provide the selected flavin cofactor moiety;

establishing in an electrochemical cell having at least the modified electrode and an auxiliary electrode, an electrolyte solution containing the biochemical substrate(s)

introducing to the electrochemical cell an enzyme suitable for catalyzing the reaction; and applying an electric potential to the electrodes sufficient to effect electron transfer between the modified electrode and the biochemical substrate through the redox active material and the enzyme.

19. A method according to claim 18 wherein the step of introducing the enzyme to the electrochemical cell comprises adding the enzyme to the electrolyte solution.

20. A method according to claim 18 wherein the step of introducing the enzyme to the electrochemical cell comprises immobilizing the enzyme on the working surface of the electrode.

21. A method according to claim 18 wherein $R_1$ is selected from the group consisting of —$CH_2(CHOH)_3CH_2OH$, —$CH_2(CHOH)_3CH_2O$—$PO_3^{2-}$, —$CH_2(CHOCOCH_3)_3CH_2OCOCH_3$, and the imidazole derivative is selected from the group consisting of the working surface of the electrode is of a material selected from the group consisting of platinum, gold, tin dioxide, silicon, graphite, glassy carbon, and conducting polymers, and the linking group is a derivative of a silane compound having the formula wherein $R_4$, $R_5$ and $R_6$ are independently selected from the group consisting of Si ligands displaceable by a hydroxide anion, and n is a positive integer from 1 to 20.

22. A method for coating an electrode substrate having a working surface of an electrically conductive or semiconductive material having an outer oxide or hydroxyl layer comprising:
electrically and covalently bonding a redox active material to the outer layer by means of a suitable linking group;
wherein the redox active material is derived from a redox active flavin derivative having the formula wherein $R_1$ is a ribose derivative and at least one of $R_2$ and $R_3$ is an imidazole derivative, the other of $R_2$ and $R_3$ being the imidazole derivative or hydrogen.

23. A method according to claim 22 wherein $R_1$ is selected from the group consisting of $-CH_2(CHOH)_3CH_2OH$, $-CH_2(CHOH)_3CH_2O-PO_3^{2-}$, $-CH_2(CHOCOCH_3)_3CH_2OCOCH_3$, and

24. A method according to claim 22 wherein the imidazole derivative is selected from the group consisting of derivatives of 25. A method of preparing a working electrode for electrochemically mediating the catalysis of a biochemical reaction by an enzyme comprising the steps of:
placing within a vessel an electrode having a working surface of an electrically conducting or semiconducting material having an outer oxide layer on the working surface;
immersing the working surface in an electrolytic solution containing a redox active material derived from a redox active flavin derivative having the formula wherein $R_1$ is a ribose derivative, at least one of $R_2$ and $R_3$ is an imidazole derivative, the other of $R_2$ and $R_3$ being the imidazole derivative or hydrogen; and a compound from which a suitable linking group may be derived, for a sufficient time to electrically and covalently bond sufficient redox active material to the outer layer by means of the linking group to provide a working electrode capable of electrochemically mediating the catalysis of the biochemical reaction.

26. A method according to claim 25 wherein the working surface of the electrode is of a material selected from the group consisting of platinum, gold, tin dioxide, silicon, graphite, glassy carbon and conducting polymers; the ribose derivative is selected from the group consisting of $-CH_2(CHOH)_3CH_2OH$, $-CH_2(CHOH)_3CH_2O-PO_3^{2-}$, $-CH_2(CHOCOCH_3)_3CH_2OCOCH_3$, and the imidazole derivative is selected from the group consisting of

-continued and the compound from which a suitable linking group may be derived is a silane compound having the formula wherein $R_4$, $R_5$, and $R_6$ are independently selected from the group consisting of Si ligands displaceable by a hydroxide anion, and n is a positive integer from 1 to 20.

27. A method according to claim 25 wherein the vessel is an electrochemical cell further containing an auxiliary electrode, and further comprising the step of establishing an electrical potential across the electrodes of sufficient density and for sufficient time to electrically and covalently bond sufficient redox active material to the outer layer by means of the linking group to provide a working electrode capable of electrochemically mediating the catalysis of the biochemical reaction.

* * * * *